United States Patent
Carrasco-Zevallos et al.

(10) Patent No.: US 10,973,405 B2
(45) Date of Patent: Apr. 13, 2021

(54) SYSTEMS AND METHODS FOR LONG WORKING DISTANCE OPTICAL COHERENCE TOMOGRAPHY (OCT)

(71) Applicant: Duke University, Durham, NC (US)

(72) Inventors: Oscar M. Carrasco-Zevallos, Durham, NC (US); Justin Migacz, Durham, NC (US); Cynthia A. Toth, Durham, NC (US); Joseph A. Izatt, Durham, NC (US)

(73) Assignee: Duke University, Durham, NC (US)

( * ) Notice: Subject to any disclaimer, the term of this patent is extended or adjusted under 35 U.S.C. 154(b) by 56 days.

(21) Appl. No.: 15/569,482

(22) PCT Filed: May 5, 2016

(86) PCT No.: PCT/US2016/031050
§ 371 (c)(1),
(2) Date: Oct. 26, 2017

(87) PCT Pub. No.: WO2016/179431
PCT Pub. Date: Nov. 10, 2016

(65) Prior Publication Data
US 2018/0296087 A1      Oct. 18, 2018

Related U.S. Application Data

(60) Provisional application No. 62/156,945, filed on May 5, 2015.

(51) Int. Cl.
*A61B 3/10* (2006.01)
*G01B 9/02* (2006.01)
*A61B 5/00* (2006.01)

(52) U.S. Cl.
CPC ............ *A61B 3/102* (2013.01); *A61B 5/0066* (2013.01); *G01B 9/02091* (2013.01)

(58) Field of Classification Search
CPC ...................................................... A61B 3/102
(Continued)

(56) References Cited

U.S. PATENT DOCUMENTS 3,272,072 A      9/1966   Ziegler
3,989,317 A  *  11/1976   Maeda ..................... G02B 9/12
                                                          359/792

(Continued)

FOREIGN PATENT DOCUMENTS

WO     WO-2013112700 A1 *  8/2013   ............ A61B 3/102

OTHER PUBLICATIONS

Lohmann, Adolf W. "Scaling Laws for Lens Systems." Applied Optics, vol. 28, No. 23, 1989, pp. 4996-4998.*

(Continued)

*Primary Examiner* — Zachary W Wilkes
(74) *Attorney, Agent, or Firm* — Olive Law Group, PLLC (57) ABSTRACT

Systems and methods for long working distance optical coherence tomography (OCT). According to an aspect, an OCT system includes a reference arm. Further, the OCT system includes a sample arm operably connected to the reference arm. The sample arm includes a scanner configured to scan an optical beam. The sample arm also includes an objective positioned a predetermined distance from the scanner, configured to receive the optical beam, and to direct the optical beam to an object positioned at about the predetermined distance from the scanner for imaging of the object.

20 Claims, 6 Drawing Sheets

(58) Field of Classification Search
USPC .................................................. 351/206, 246
See application file for complete search history.

(56) References Cited

U.S. PATENT DOCUMENTS

| | | | |
|---|---|---|---|
| 7,177,491 B2 | 2/2007 | Dave et al. | |
| 7,695,137 B2* | 4/2010 | Fercher | A61B 3/102 |
| | | | 351/205 |
| 8,783,866 B2 | 7/2014 | Hart et al. | |
| 8,896,842 B2 | 11/2014 | Bower et al. | |
| 10,076,243 B2* | 9/2018 | Murata | A61B 3/1025 |
| 2009/0268161 A1* | 10/2009 | Hart | A61B 3/102 |
| | | | 351/208 |
| 2011/0102802 A1* | 5/2011 | Izatt | A61B 3/102 |
| | | | 356/479 |

OTHER PUBLICATIONS

Griot, Melles. "Achromatic Doublets." Melles Griot Product Catalogue, 1999, pp. 7.1-7.13.*
Carrasco-Zevallos, Oscar M et al. "Long working distance OCT with a compact 2f retinal scanning configuration for pediatric imaging." Optics letters vol. 41,21 (2016): 4891-4894. doi:10.1364/OL.41.004891 (Year: 2016).*
International Search Report and Written Opinion issued in PCT Application No. PCT/US2016/031050 dated Aug. 12, 2016.
International Preliminary Report on Patentability issued in counterpart PCT Application No. PCT/US2016/031050 dated Nov. 7, 2017 (nine (9) pages).

* cited by examiner

FIG. 3A  AR: 8.86  +5 D Correction

FIG. 3B  AR: 9.85  0 D Correction

FIG. 3C  AR: 11.69  -8 D Correction

SYSTEMS AND METHODS FOR LONG WORKING DISTANCE OPTICAL COHERENCE TOMOGRAPHY (OCT)

CROSS REFERENCE TO RELATED APPLICATION

This is a 371 national stage patent application, which claims priority to PCT International Patent Application No. PCT/US2016/031050, filed May 5, 2016, and titled SYSTEMS AND METHODS FOR LONG WORKING DISTANCE OPTICAL COHERENCE TOMOGRAPHY (OCT), which claims the benefit of U.S. Provisional Patent Application No. 62/156,945, filed May 5, 2015, and titled SYSTEMS AND METHODS FOR LONG WORKING DISTANCE OPTICAL COHERENCE TOMOGRAPHY, the disclosures of which are incorporated herein by reference in their entireties.

FEDERALLY SPONSORED RESEARCH OR DEVELOPMENT

The technology disclosed herein was made in part with government support under Federal Grant No. R01-EY023039 awarded by the National Institutes of Health (NIH). The United States government has certain rights in the technology.

TECHNICAL FIELD

The present subject matter relates to medical imaging. More particularly, the present subject matter relates to systems and methods for long working distance optical coherence tomography (OCT).

BACKGROUND

OCT has become the standard of care for diagnosis of many retinal pathologies. However, current generation commercial OCT systems require a skilled operator and cooperative subjects to obtain and maintain subject alignment and fixation for several seconds in a chinrest. Handheld OCT systems have also been demonstrated for successful imaging of supine patients, as well as pre-term infants and neonates up to about one year old. However, current OCT technology is lacking for use with young children due to their lack of attention and cooperation, as well as inherent fear of strangers placing such large equipment close to their faces. Current OCT systems are also unsuitable in potential applications for consumer imaging and/or screening in retail environments such as booths or shopping centers, where skilled operators may not be available. For at least these reasons, there is a need for improved OCT systems and methods for use with young children.

SUMMARY

Disclosed herein are systems and methods for long working distance OCT. According to an aspect, an OCT system includes a reference arm. Further, the OCT system includes a sample arm operably connected to the reference arm. The sample arm includes a scanner configured to scan an optical beam. The sample arm also includes an objective positioned a predetermined distance from the scanner, configured to receive the optical beam, and to direct the optical beam to an object positioned at about the predetermined distance from the scanner for imaging of the object.

BRIEF DESCRIPTION OF THE DRAWINGS

The foregoing aspects and other features of the present subject matter are explained in the following description, taken in connection with the accompanying drawings, wherein.

DETAILED DESCRIPTION

For the purposes of promoting an understanding of the principles of the present disclosure, reference will now be made to various embodiments and specific language will be used to describe the same. It will nevertheless be understood that no limitation of the scope of the disclosure is thereby intended, such alteration and further modifications of the disclosure as illustrated herein, being contemplated as would normally occur to one skilled in the art to which the disclosure relates.

Articles "a" and "an" are used herein to refer to one or to more than one (i.e. at least one) of the grammatical object of the article. By way of example, "an element" means at least one element and can include more than one element.

In this disclosure, "comprises," "comprising," "containing" and "having" and the like can have the meaning ascribed to them in U.S. Patent law and can mean "includes," "including," and the like; "consisting essentially of" or "consists essentially" likewise has the meaning ascribed in U S. Patent law and the term is open-ended, allowing for the presence of more than that which is recited so long as basic or novel characteristics of that which is recited is not changed by the presence of more than that which is recited, but excludes prior art embodiments.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

Unless specifically stated or obvious from context, as used herein, the term "about" is understood as within a range of normal tolerance in the art, for example within 2 standard deviations of the mean. The term "about" can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term "about."

Unless otherwise defined, all technical terms used herein have the same meaning as commonly understood by one of ordinary skill in the art to which this disclosure belongs.

The present disclosure provides, in part, an OCT system, and methods of using the system, that utilizes a very long working distance. As described herein, the "working distance" refers to the distance between the last optical component of the system and a subject's eye. This system can facilitate imaging of subjects under conditions when conventional tabletop or handheld OCT systems are impractical, such as for imaging subjects in retail or consumer outlets or for imaging young children. The OCT system can achieve a working distance of about 35 centimeters or another suitable distance to situate subjects at a comfortable distance away during imaging. In accordance with embodiments of the present disclosure, a 2f retinal OCT scanning configuration with a suitable optical design is described herein for reducing the footprint and weight of the sample arm. Swept-source OCT technology, in conjunction with GPU-based software, can enable fast volumetric imaging and real time rendering at 100 kHz A-line rate.

Figure 1:
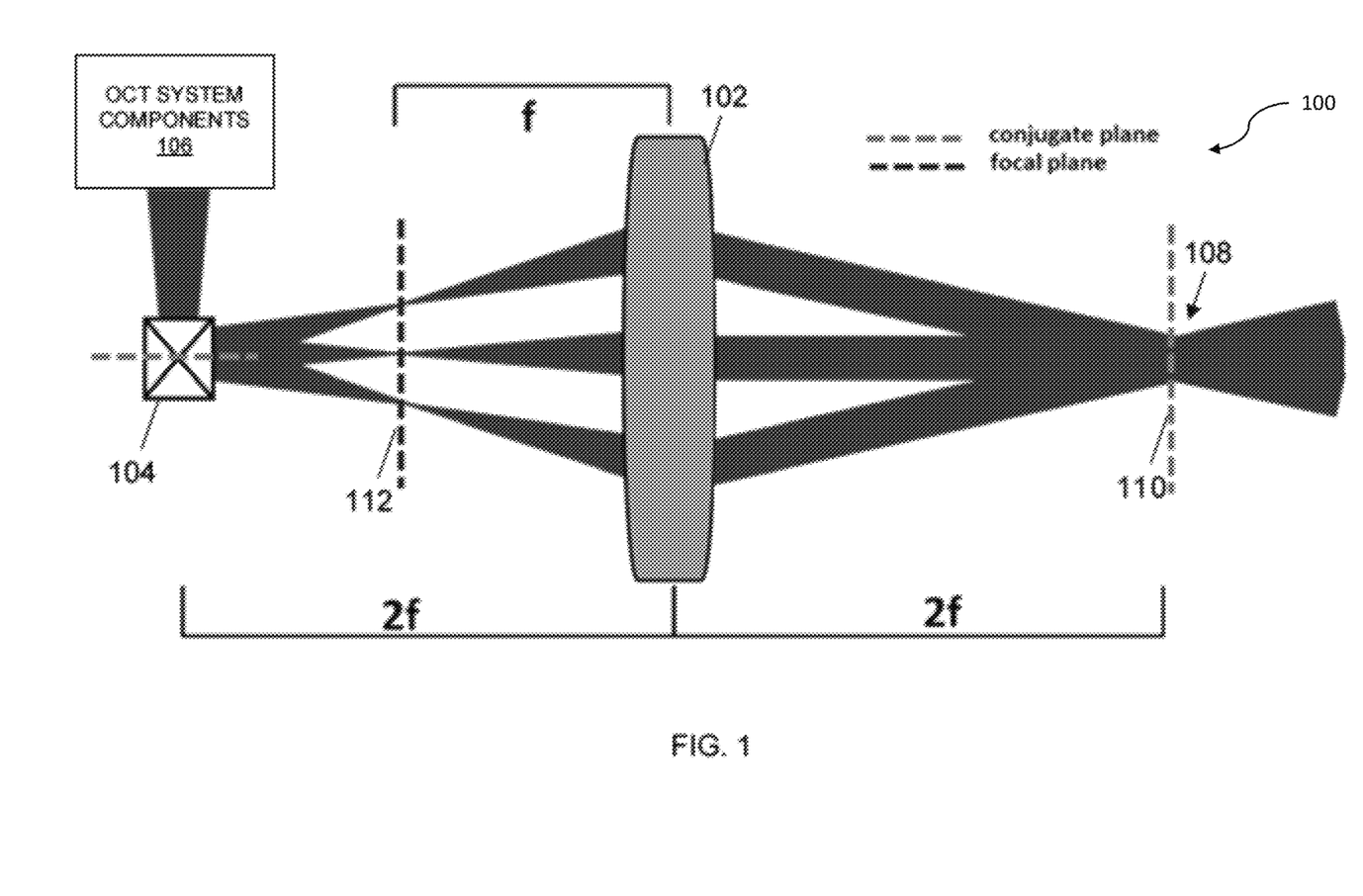
FIG. 1 is a schematic diagram of an example 2f optical scanning configuration for use in an OCT system for retinal imaging in accordance with embodiments of the present disclosure.

In accordance with embodiments of the present disclosure, retinal scanning configuration OCT systems are disclosed for achieving a suitable working distance. For example, FIG. 1 illustrates a schematic diagram of an example 2f optical scanning configuration for use in an OCT system for retinal imaging in accordance with embodiments of the present disclosure. The configuration shown in FIG. 1 has a working distance of about 35 centimeters such that subjects can be situated at a comfortable distance away during imaging. The configuration can be beneficial in that it reduces the footprint and weight of the sample arm in comparison to other systems. Referring to FIG. 1, the configuration includes a sample arm (generally designated 100) having an objective 102, a scanner 104, and other OCT system components 106 for capturing images of an object (positioned generally at 108) and for subsequent processing of the captured images.

The scanner 104 is placed a distance 2f away from the objective 102. The scanner may include a scanning mirror or mirrors. The objective 102 may be a single or compound lens, and is the component of the OCT system placed closest to the subject's eye. Converging light incident on the scanning mirrors may be arranged by an additional converging lens arranged to focus the scanned sample arm beam approximately one focal length in front of the objective 102 (i.e., midway between the scanning mirrors and the lens), resulting in collimated light incident on a subject's cornea in the application of retinal imaging.

The subject's pupil may be placed 2f away from the objective 102 and may thus be conjugate with the scanning mirrors, as shown by dashed line 110. This 2f design can result in a reduced number of lenses required to relay the scanning mirror pivot to the patient's pupil, resulting in compact, cost reduced optical design. Moreover, this configuration is capable of long working distances with comparatively shorter focal length lenses. Significantly, with this configuration the working distance is equal to approximately twice the focal length of the objective lens (the last lens before the subject's eye), rather than approximately equal to the focal length of the objective lens as in previous OCT retinal scanning configurations. The focal plane location is depicted by dashed line 112.

Figure 2A:
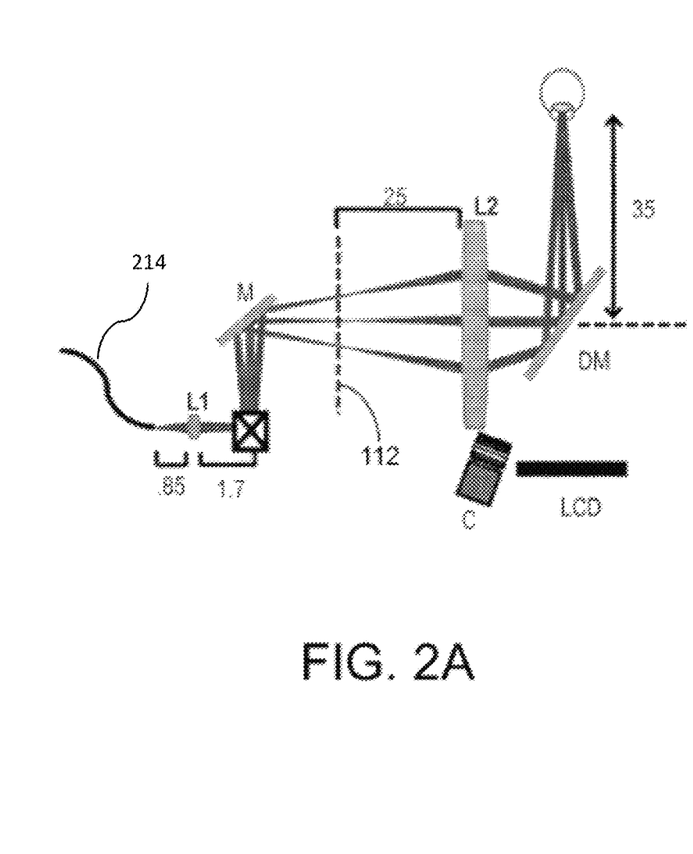
FIG. 2A is a schematic diagram of an example OCT sample arm of an OCT system having a long working distance in accordance with embodiments of the present disclosure.

To achieve a near diffraction-limited lateral resolution at the retinal plane with a long working distance (e.g., 35 centimeters), a 2f system may employ two lenses L1 (converging lens) and L2 (objective lens) as depicted in FIG. 2A. FIG. 2A illustrates a schematic diagram of an example OCT sample arm of an OCT system having a long working distance in accordance with embodiments of the present disclosure. The dimensions of the OCT sample arm shown in FIG. 2A are given in centimeters. In an implementation, the objectives L1 and L2 were manufactured by Zemax, Inc. of Redmond, Wash. The number of elements, diameter thickness, and surface curvatures of objectives L1 and L2 may be suitably optimized to minimize aberrations while optimizing for cost-effectiveness using a schematic eye. Alternatively, for example, the optical function of converging lens L1 may be separated into two separate lenses, one for the purpose of collimating light from the sample arm optical fiber (as in a conventional OCT retinal scanner) and a second converging lens to focus the scanned light beam between the scanner and the objective lens.

The sample arm shown in FIG. 2A includes a dichroic mirror (DM) to reflect OCT imaging light while enabling the subject to view a fixation target screen (LCD). This example optical design can achieve a working distance of about 35 cm. To facilitate alignment, an iris camera (c) may be used. (C) photograph of the sample arm optics.

Figure 2B:
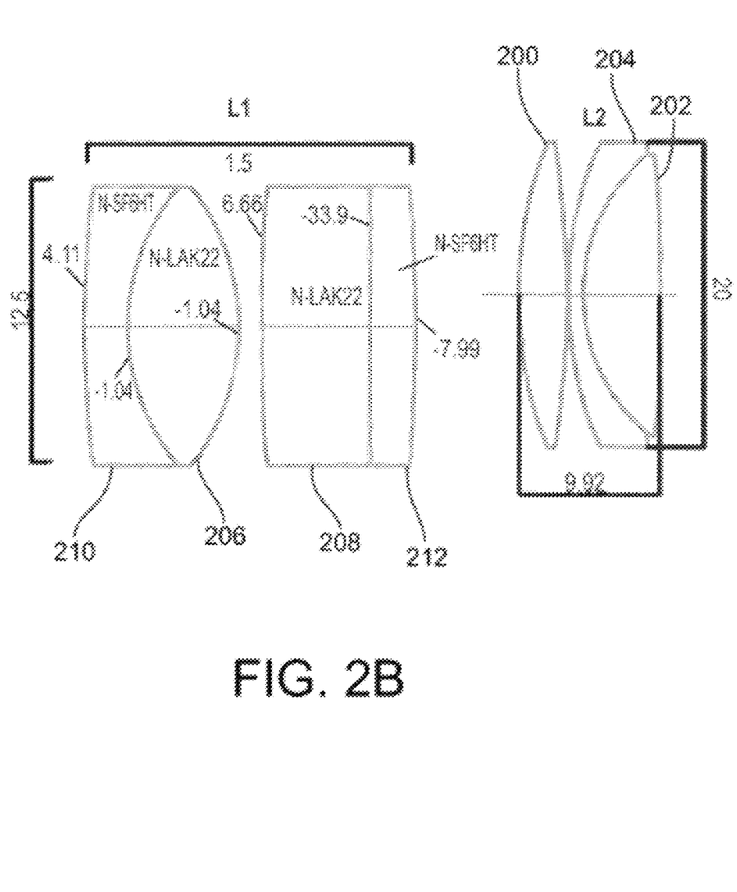
FIG. 2B is diagrams of example objectives L1 and L2 that may be used in the sample arm shown in FIG. 2A or another suitable sample arm in accordance with embodiments of the present disclosure.

FIG. 2B illustrates diagrams of example lenses L1 and L2 that may be used in the sample arm shown in FIG. 2A or another suitable sample arm in accordance with embodiments of the present disclosure. The dimensions of the example lenses shown in FIG. 2B are given in centimeters. Referring to FIG. 2B, objective L2 includes 2 positive elements 200 and 202 and a negative element 204 to reduce chromatic aberrations. In this example, the positive elements 200 and 202 are a convex lens and a piano convex lens, respectively. Also in this example, the negative element 204 is a negative meniscus lens. The diameter of the objective L2 is about 20 cm in diameter, with a total thickness of about 9.92 cm and an effective focal length of about 50 cm.

Objective L1 includes 2 positive elements 206 and 208 and 2 negative elements 210 and 212. In this example, objective L1 has a total thickness of about 15 mm and a diameter of about 12.5 mm. Due to the size and weight of objective L2, compensating for refractive error by axially displacing the objective may be unfeasible. Instead, the distance between a fiber terminator, such as fiber terminator 214 shown in FIG. 2A, and objective L1 may be varied to change the focal plane (shown be dashed line 112) prior to objective L2 and thus the vergence of the rays prior to the subject's cornea. In this example, the optical design was optimized for −8D to +5D correction to ensure near diffraction limited error after correction for the subject's refractive error. A dichroic mirror after the objective can enable co-alignment of a LCD display used for fixation. The monitor displayed videos and targets to aid fixation during imaging. The system achieved a field of view of +/−8 degrees.

Figure 3A:
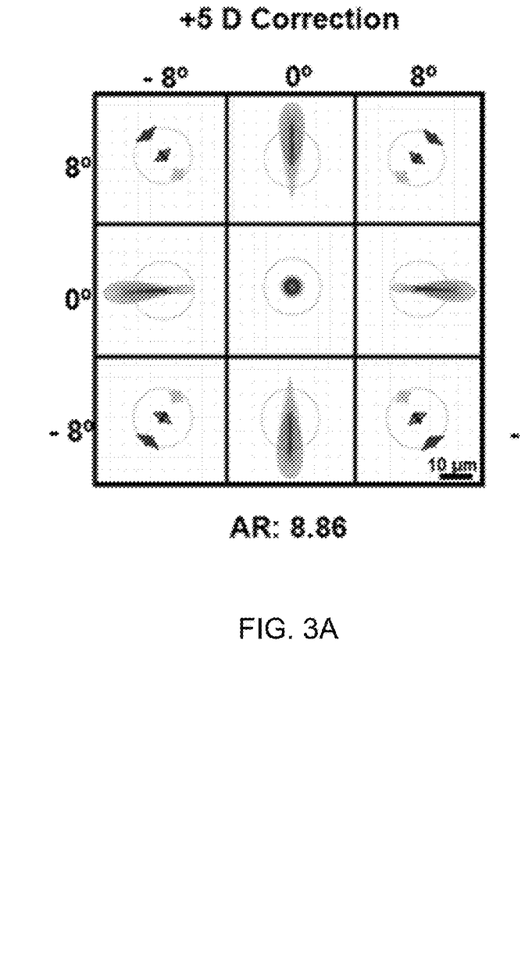
FIGS. 3A-3C are images showing theoretical optical performance of a system at three different refractive correction configurations in accordance with embodiments of the present disclosure.
Figure 3B:
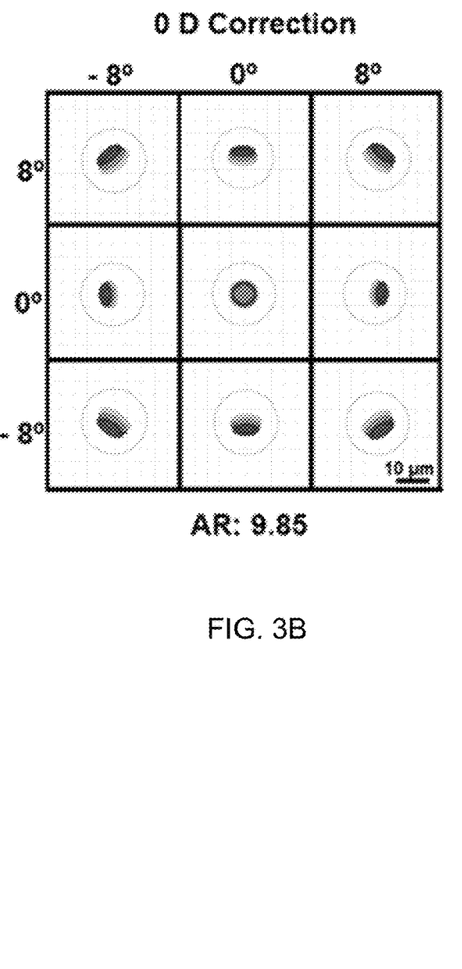
Figure 3C:
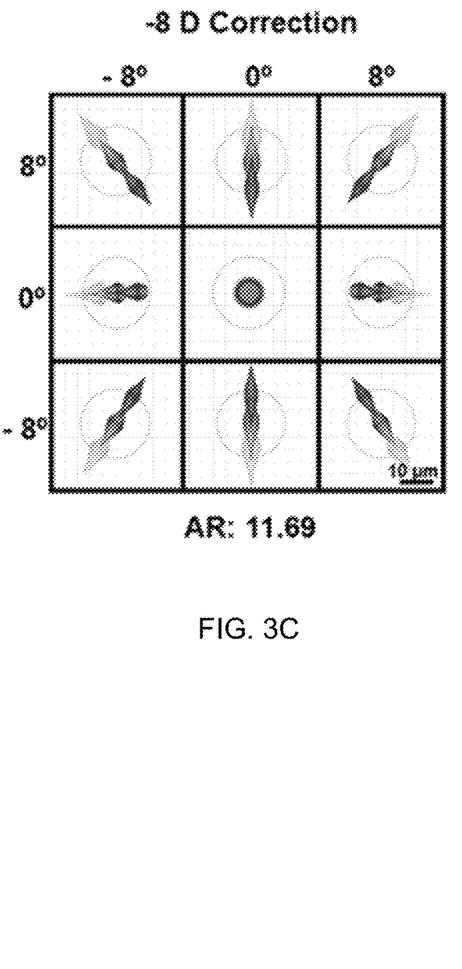

FIGS. 3A-3C depict images showing theoretical optical performance of a system at three different refractive correction configurations in accordance with embodiments of the present disclosure. All unspecified dimensions are in microns. "AR" in the figures is the airy disk radius. The theoretical optical performance of the system predicted by ray tracing software is shown in FIGS. 3A-3C for three different configurations: +5 D, 0 D, and −8 D corrections. Retinal plane spot diagrams at the extreme points of the field of view for each configurations are shown. The different shades of grayscale represent different wavelengths (1.0, 1.06, and 1.1 μm) of the broadband source. At 0 D correction, the system achieves diffraction limited resolution of 9.85 μm throughout the entire field of view. At +5 and −8 D correction, the system achieves near diffraction limited resolutions of 8.86 μm and 11.69 μm, respectively. However, at these configurations, lateral, axial, and spherical aberrations are prominent, as determined by the Seidel coefficients in ray tracing software, and may result in an asymmetric, albeit near diffraction limited, PSF.

Figures 4A, 4B:
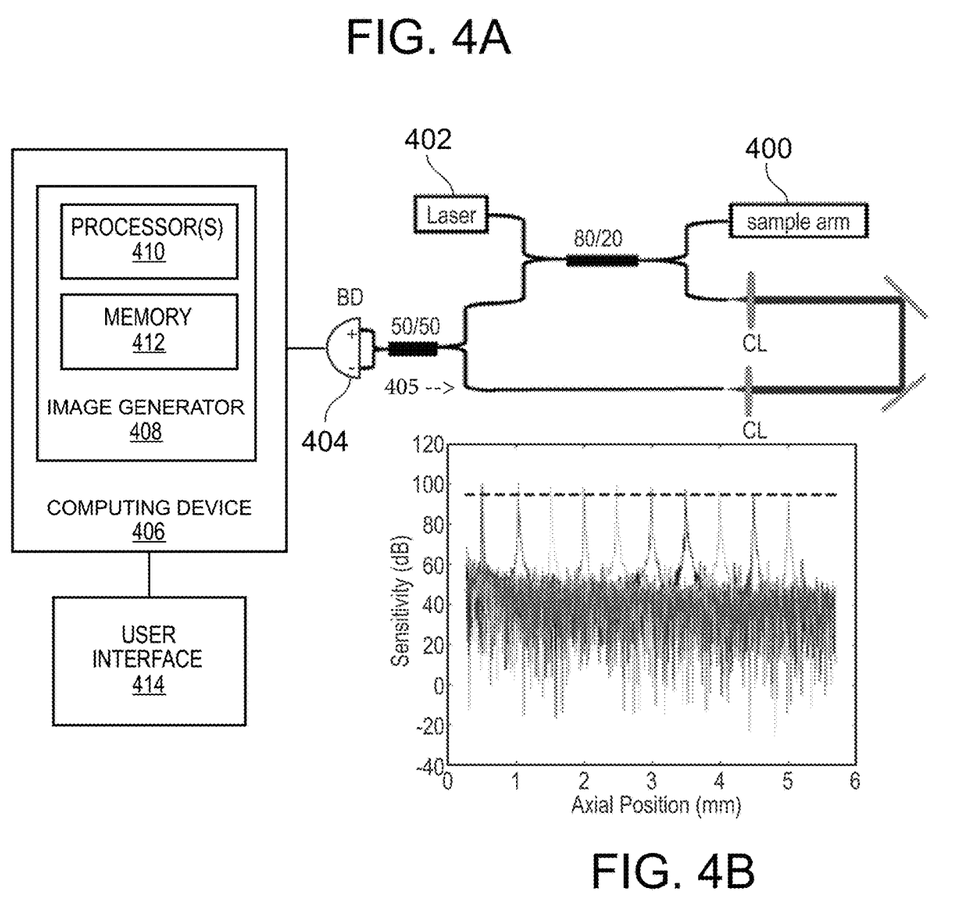
FIG. 4A is schematic diagram of an example OCT system in accordance with embodiments of the present disclosure.
FIG. 4B is a graph showing sensitivity fall off performance in accordance with one embodiment of the present disclosure.

FIG. 4A is a schematic diagram of an example OCT system in accordance with embodiments of the present disclosure. Referring to FIG. 4A, the OCT system includes a sample arm 400, which may include the components of the sample arm shown in FIG. 2A and may be configured to operate therewith as will be understood to those of skill in the art. The OCT system may be a swept-source OCT system employing a 1060 nm frequency-swept laser 402 (e.g., a suitable laser provided by Axsun Tech of Billerica, Mass.) and a Mach-Zender interferometer as depicted in FIG. 4A. A dual-balanced receiver and digitizer 404 may detect the interferometric signal. As an example, the dual-balanced receiver may be provided by Thorlabs, Inc. of Newton, N.J. The digitizer may digitize at 800 MS/s or another suitable rate. In an example, GPU-based software may enable real-time volumetric imaging at 100,000 A-line/s. The peak sensitivity of the system may be measured at 100.8 dB. Sensitivity fall off was −6 dB at 4.5 mm. The average axial resolution was 8.4 μm across the entire depth range of 3.7 mm. Components of the reference arm are generally designated by arrow 405.

The dual-balanced receiver and digitizer 404 may be operably connected to a computing device 406. The computing device 406 may be configured to receive capture image data from the dual-balanced receiver and digitizer 404. The computing device 406 may be a desktop computer, a laptop computer, a tablet computer, a smartphone, or the like configured to implement the functionality described herein. Particularly, the computing device 406 may include an image generator 408 configured to generate images for view by an operator. The image generator 408 may be implemented by hardware, software, firmware, or combinations thereof. For example, the image generator 408 may include one or more processors 410 and memory 412. The memory 412 may store instructions for execution by the processor(s) 410 for implementing the functionality disclosed herein. Particularly, the image generator 408 can generate one or more images or video of the subject based on the received image data. Further, the image generator 408 can control the display of images on a display of a user interface 414.

Figure 5A:
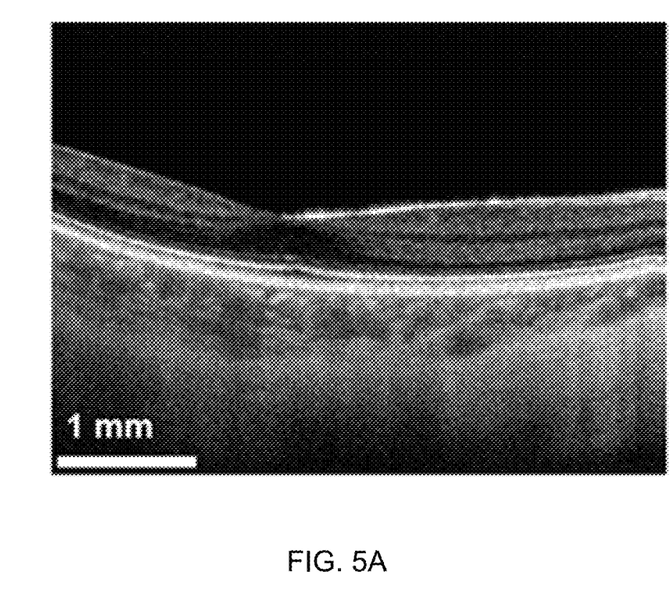
FIGS. 5A and 5B are images of a representative averaged B-scan image (500 A-scans/B-scans, averaged 10×) and volumetric image (500 A-scans/B-scan, 128 B-scans/volume), respectively.
Figure 5B:
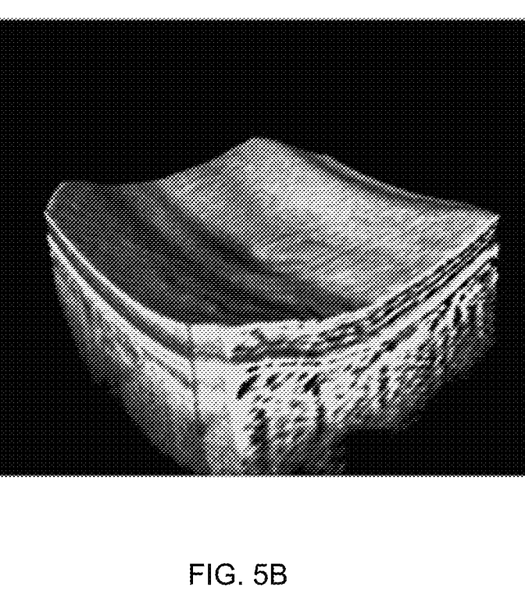

To prove the feasibility of the system, consented adult subjects were imaged. The optical power incident on the cornea was 1.9 mW, consistent with ANSI safety standards at this wavelength. FIGS. 5A and 5B show images of a representative averaged B-scan image (500 A-scans/B-scans, averaged 10×) and volumetric image (500 A-scans/B-scan, 128 B-scans/volume), respectively. The subject was situated on a chin rest 35 cm away from the system. The LCD monitor and iris camera facilitated fixation during imaging. The volumetric scan was acquired, processed, and rendered in real time.

Figure 6:
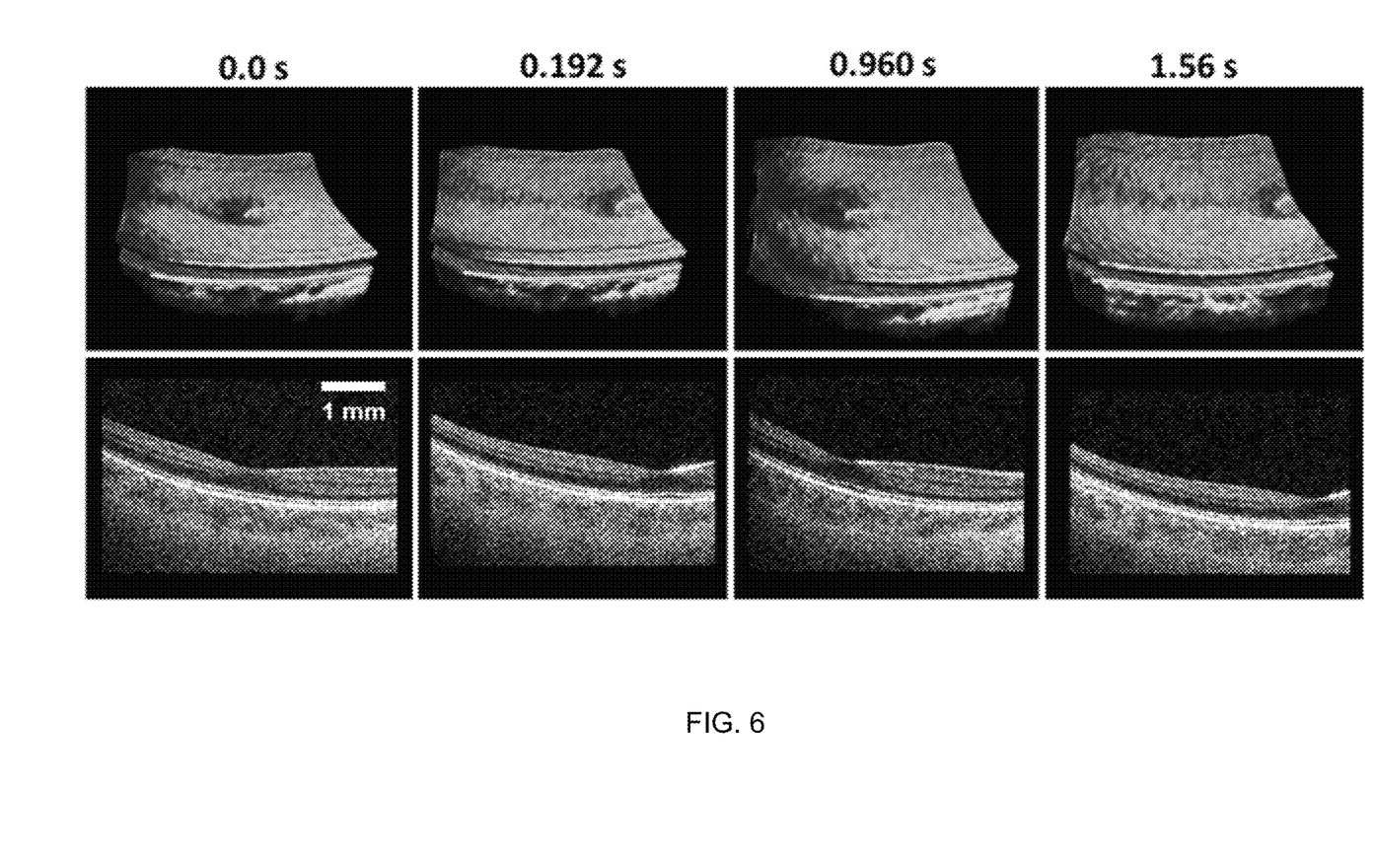
FIG. 6 depicts a volumetric time series of a subject fixating at two different targets.

To demonstrate fast volumetric imaging, a series of volumes were obtained from a subject alternating fixation between two laterally displaced targets. The volumetric acquisition rate was 5.21 volumes/second. Each volume was composed of 300 A-scans/B-scans and 64 B-scans/volume and was rendered in real time. The volumetric time series is shown in FIG. 6, with time stamps referenced to the first frame. Corresponding, single frame B-scans centered at the fovea are shown below. The time series data show the subject's fovea moving laterally as the fixation point is changed.

FIG. 6 depicts a volumetric time series of a subject fixating at two different targets. Lateral displacement of the fovea is evident in both the volumes and corresponding B-scans.

The various techniques described herein may be implemented with hardware or software or, where appropriate, with a combination of both. Thus, the methods and apparatus of the disclosed embodiments, or certain aspects or portions thereof, may take the form of program code (i.e., instructions) embodied in tangible media, such as floppy diskettes, CD-ROMs, hard drives, or any other machine-readable storage medium, wherein, when the program code is loaded into and executed by a machine, such as a computer, the machine becomes an apparatus for practicing the presently disclosed subject matter. In the case of program code execution on programmable computers, the computer will generally include a processor, a storage medium readable by the processor (including volatile and non-volatile memory and/or storage elements), at least one input device and at least one output device. One or more programs may be implemented in a high level procedural or object oriented programming language to communicate with a computer system. However, the program(s) can be implemented in assembly or machine language, if desired. In any case, the language may be a compiled or interpreted language, and combined with hardware implementations.

The described methods and apparatus may also be embodied in the form of program code that is transmitted over some transmission medium, such as over electrical wiring or cabling, through fiber optics, or via any other form of transmission, wherein, when the program code is received and loaded into and executed by a machine, such as an EPROM, a gate array, a programmable logic device (PLD), a client computer, a video recorder or the like, the machine becomes an apparatus for practicing the presently disclosed subject matter. When implemented on a general-purpose processor, the program code combines with the processor to provide a unique apparatus that operates to perform the processing of the presently disclosed subject matter.

Features from one embodiment or aspect may be combined with features from any other embodiment or aspect in any appropriate combination. For example, any individual or collective features of method aspects or embodiments may be applied to apparatus, system, product, or component aspects of embodiments and vice versa.

While the embodiments have been described in connection with the various embodiments of the various figures, it is to be understood that other similar embodiments may be used or modifications and additions may be made to the described embodiment for performing the same function without deviating therefrom. Therefore, the disclosed embodiments should not be limited to any single embodiment, but rather should be construed in breadth and scope in accordance with the appended claims. One skilled in the art will readily appreciate that the present subject matter is well adapted to carry out the objects and obtain the ends and advantages mentioned, as well as those inherent therein. The present examples along with the methods described herein are presently representative of various embodiments, are exemplary, and are not intended as limitations on the scope of the present subject matter. Changes therein and other uses will occur to those skilled in the art which are encompassed within the spirit of the present subject matter as defined by the scope of the claims.

What is claimed:

1. An optical coherence tomography (OCT) system comprising:
    a reference arm; and
    a sample arm operably connected to the reference arm and comprising:
        a scanner configured to scan an optical beam along a first optical pathway;
        an objective positioned a predetermined distance from the scanner along the first optical pathway, wherein the objective is configured to receive the optical beam along the first optical pathway, and wherein the objective is configured to direct the optical beam to an object positioned along a second optical pathway for imaging of the object, wherein a distance between the objective and the object is about the same distance as the predetermined distance, wherein the predetermined distance is approximately equal to twice the focal length of the objective, and wherein the objective relays collimated light to the object that is placed a distance of twice a focal length of the objective away from the objective;
        a dichroic mirror positioned along the second optical pathway, wherein the dichroic mirror is configured to reflect object imaging light and to permit viewing of a display screen; and
        a converging lens configured to focus the scanned optical beam approximately one focal length of the objective in front of the objective.

2. The OCT system of claim 1, wherein the objective comprises a negative meniscus lens, a convex lens, and a plano convex lens, wherein a total thickness of the negative meniscus lens, the convex lens, and the plano convex lens is about 10 centimeters.

3. The OCT system of claim 1, wherein the object is a patient's eye,
    wherein the system further comprises scanning mirrors, and
    wherein the scanning mirrors and a pupil plane of the patient's eye are conjugate to one another, and angular fields generated by the scanning mirrors are relayed to the subject's pupil.

4. The OCT system of claim 1, wherein the object is an eye.

5. The OCT system of claim 1, wherein the objective is configured to receive an image of the object and to direct the image towards the scanner.

6. The OCT system of claim 1, wherein the scanner is one of one or more galvanometer scanning mirrors or resonant scanning mirrors.

7. The OCT system of claim 1, wherein the predetermined distance ranges between 2.5 to 50 centimeters.

8. The OCT system of claim 1, wherein the sample arm comprises:
    a fiber including a terminator; and
    wherein the converging lens is positioned between the scanner and the terminator of the fiber for focusing light passing through the scanner approximately a focal length of the objective in front of the objective, and for focusing images of the object received from the scanner into the terminator of the fiber.

9. The OCT system of claim 8, further comprising scanning mirrors, and
    wherein the lens comprises two achromatic lenses and relays converging light onto the scanning mirrors.

10. The OCT system of claim 1, further comprising:
    a photoreceiver and digitizer configured to receive the image of the object and to generate data representative of the image; and
    an image generator configured to display the image based on the generated data.

11. A method for optical coherence tomography (OCT) imaging, the method comprising:
    providing an OCT system comprising:
        a reference arm; and
        a sample arm operably connected to the reference arm and comprising:
            a scanner configured to scan an optical beam along a first optical pathway; and
            an objective positioned a predetermined distance from the scanner along the first optical pathway using the scanner to scan an optical beam;
        a dichroic mirror positioned along with second optical pathway, wherein the dichroic mirror is configured to reflect object imaging light and to permit viewing of a display screen; and
    a converging lens configured to focus the scanned optical beam approximately one focal length of the objective in front of the objective; and
    receiving, at the objective, the optical beam; and
    using the objective to direct the optical beam to an object positioned along a second optical pathway for imaging of the object, wherein a distance between the objective and the object is about the same distance as the predetermined distance, wherein the predetermined distance is approximately equal to twice the focal length of the objective, and wherein the objective relays collimated light to the object that is placed a distance of twice a focal length of the objective away from the objective.

12. The method of claim 11, wherein the objective comprises a negative meniscus lens, a convex lens, and a plano convex lens, wherein a total thickness of the negative meniscus lens, the convex lens, and the plano convex lens is about 10 centimeters.

13. The method of claim 11, wherein the object is a patient's eye,
    wherein the OCT system further comprises scanning mirrors
    wherein the scanning mirrors and a pupil plane of the patient's eye are conjugate to one another, and angular fields generated by the scanning mirrors are relayed to the subject's pupil.

14. The method of claim 11, wherein the object is an eye.

15. The method of claim 11, wherein the objective is configured to receive an image of the object and to direct the image towards the scanner.

16. The method of claim 11, wherein the scanner is one of one or more galvanometer scanning mirrors or resonant scanning mirrors.

17. The method of claim 11, wherein the predetermined distance ranges between 2.5 to 50 centimeters.

18. The method of claim 11, wherein the sample arm comprises:

a fiber including a terminator; and wherein the converging lens is positioned between the scanner and the terminator of the fiber for focusing light passing through the scanner approximately a focal length of the objective in front of the objective lens, and for focusing images of the object received from the scanner into the terminator of the fiber.

19. The method of claim 18, further comprising scanning mirrors wherein the lens comprises two achromatic lenses and relays converging light onto the scanning mirrors.

20. The method of claim 11, further comprising:

a photoreceiver and digitizer configured to receive the image of the object and to generate data representative of the image; and an image generator configured to display the image based on the generated data.

\* \* \* \* \*